United States Patent [19]

Hermolin

[11] Patent Number: 4,925,967

[45] Date of Patent: May 15, 1990

[54] PROCESS FOR THE PREPARATION OF 2,2-DIBROMONITRILOPROPIONAMIDE

[75] Inventor: Joshua Hermolin, Ramat Hasharon, Israel

[73] Assignee: Bromine Compounds Limited, Israel

[21] Appl. No.: 241,493

[22] Filed: Sep. 7, 1988

[30] Foreign Application Priority Data

Sep. 15, 1987 [IL] Israel .................................. 83902

[51] Int. Cl.$^5$ ...................................... C07C 121/417
[52] U.S. Cl. ................................................ 558/445
[58] Field of Search .......................... 558/445; 514/528

[56] References Cited

U.S. PATENT DOCUMENTS

| | | | |
|---|---|---|---|
| 3,403,174 | 9/1968 | Chance et al. | 558/445 |
| 3,488,734 | 1/1970 | Burk | 558/445 |
| 3,493,658 | 2/1970 | Schmidt et al. | 514/528 X |
| 3,751,444 | 8/1973 | Solem et al. | 558/445 |
| 4,232,041 | 11/1980 | Burk et al. | 514/212 X |
| 4,328,171 | 5/1982 | Burk et al. | 558/445 X |

Primary Examiner—Joseph Paul Brust
Attorney, Agent, or Firm—Lerner, David, Littenberg, Krumholz & Mentlik

[57] ABSTRACT

A process is disclosed for the preparation of 2,2-dibromonitrilopropionamide, in which cyanoacetamide is brominated in aqueous medium with bromine or hydrobromic acid, in the presence of an oxidizing agent and at elevated temperature, followed by cooling of the reaction mixture to precipitate the DBNPA.

14 Claims, No Drawings

PROCESS FOR THE PREPARATION OF 2,2-DIBROMONITRILOPROPIONAMIDE

The present invention relates to a process for the preparation of 2,2-dibromonitrilopropionamide (DBNPA). More particularly, the invention relates to a process in which DBNPA is obtained by the bromination of cyanoacetamide (CAA) in aqueous medium.

DBNPA is a well known biocide, useful in numerous industrial and agricultural applications, and many processes for its preparation are known in the art. Its preparation by the reaction of bromine and CAA in aqueous medium has been known for a long time [G. Fels, Z. Kryst. 32, 359 (1900)]. However, the processes known in the art present several severe drawbacks. For instance, in the process described by Fels half of the bromine is converted into HBr, leading to the waste of valuable bromides and resulting in corrosive mixtures which require the use of expensive construction materials. The art has attempted to solve these problems in different ways.

British Patent No. 1,103,391 describes the use of sodium acetate to convert HBr into NaBr, which solves the corrosion problem but not that of bromide loss.

U.S. Pat. No. 3,751,444 discloses a process in which sodium bromate ($NaBrO_3$) is employed to convert the HBr formed in the reaction into $Br_2$. The process is carried out at temperatures between the freezing point of the mixture and 40° C. for several hours. According to the teachings of this patent 40° C. is the maximum operating temperature, because of hydrolysis limitations. This patent also teaches that other water soluble oxidizing agents, such as $H_2O_2$, $NaClO_3$, $NaNO_3$, $NaClO$ and $NaClO_4$, react at least one order of magnitude slower than $NaBrO_3$.

Israeli Patent 46112 discloses the use of $NaClO_3$ and mineral acids, such as HCl and $H_2SO_4$. This process leads to the presence of NaCl and of salts of the mineral acid, which must be washed off the product and be treated prior to the disposal of the mother liquor. A similar process is described in Spanish Patent No. 549,319.

It has now been found, and this is an object of the invention, that it is possible to provide a very efficient and waste-free process for the preparation of DBNPA, which does not result in the accumulation of any undesirable by-product such as the sodium salts obtained in the processes of the art.

It has further surprisingly been found, and this is another object of the invention, that contrary to the teachings of the art it is possible to prepare DBNPA at elevated temperatures, such as 70° C. and higher, while avoiding excessive hydrolytic side-reactions, to provide a pure product with a very high yield. Surprisingly, $H_2O_2$ can be employed as the oxidizing agent, to regenerate $Br_2$ from HBr produced in the reaction, thereby exploiting substantially all the bromine fed to the reactor. Very high reaction rates are obtained when operating according to the invention.

The process for the preparation of 2,2-dibromonitrilopropionamide (DBNPA) according to the invention is characterized in that cyanoacetamide is reacted in aqueous medium with bromine or hydrobromic acid, in the presence of hydrogen peroxide, at an elevated temperature, as hereinafter defined, and the reaction mixture is then cooled to a low temperature to precipitate DBNPA.

By elevated temperature is meant temperatures equal to or greater than about 70° C., at which temperature the reaction mixture is substantially homogeneous. Of course, the upper limit of the reaction temperature will, for practical purposes, be the boiling point of the reaction mixture. Although temperatures lower than 70° C. can be employed, they result in longer residence-times, and as will be apparent to the skilled engineer, will increase the extent of undesired hydrolytic side reactions. For this reason, the reaction is preferably carried out at a temperature comprised between about 80° C. and about 100° C.

For the same reason, as well as to obtain a precipitation of the product, the reaction mixture is quickly cooled down to a low temperature. This low temperature should be chosen to be such that hydrolysis does not proceed to any appreciable extent. Typically, this will occur at room temperature or slightly lower, viz., about 0°–30° C.

Commonly, the duration of reaction should be shorter than 30 minutes, preferably shorter than 10 minutes.

Contrary to the processes known in the art, no accumulation of salts or foreign products occur in the process of the invention. Therefore, the mother liquor can be recycled and reactants are added to it, without any treatment. This can be continued indefinitely, at least theoretically, with only a minor bleed which substantially corresponds to the amount of water formed in the reaction, if steady state conditions are to be maintained and the total volume of mother liquor maintained constant.

According to the invention, a virtually waste-free process can be carried out, because the mother liquor, or any portion thereof which is not recycled into the reaction vessel, is employed as the basis for a liquid formulation of DBNPA, usually by adding to it additional amounts of solid DBNPA and/or additives. Such liquid formulations are known in the art to be useful for a number of applications, as described, e.g., in U.S. Pat. No. 4,232,041 and Israeli Patent 65419. Aqueous DBNPA solutions, whenever obtained by the process of the invention, also form part of the present invention.

According to a preferred embodiment of the invention the reaction of $Br_2$, hydrogen peroxide and cyanoacetamide is carried out in a continuous mode, more preferably with recycle of mother liquor, as detailed above. When operating with such recycle, yields of DBNPA of 95% or higher are obtained after three reaction cycles. However, as said, the total yield is practically quantitative, since the excess mother liquor can be suitably employed to provide liquid DBNPA formulations.

As will be apparent to a person skilled in the art, it is important to effect the addition of $H_2O_2$ to the reaction mixture after some HBr is already present in the mother liquor, to avoid undesirable reactions of the peroxide in the reaction mixture. This, however, can be easily achieved by delaying the addition of the peroxide, e.g., to the second production cycle, since in any case a number of cycles will be necessary before steady state is attained. A skilled person could also envisage the addition of a mineral acid as a source of H+ ions, to accelerate the oxidation reaction of the bromide to bromine. However, the addition of a mineral acid, while possible, is not advantageous in the process of the invention, since excess HBr can be obtained at will in the mother liquor, simply by adding HBr or by delaying the addition of hydrogen peroxide until the desired H+ concentration is obtained.

It should be understood that the advantage of operating the process for producing DBNPA at high temperatures - for very short reaction times - is not limited to processes employing $H_2O_2$ as an HBr oxidation agent. Other water soluble oxidants, such as $NaBrO_3$, $NaClO_3$ or the like agents, which are known in the art and which will be recognized by the skilled chemist, can likewise be exploited under similar conditions. However, when such oxidizing agents are employed instead of $H_2O_2$ the accumulation of the corresponding metal salt in the reaction medium is unavoidable.

The above and other characteristics and advantages of the invention will be better appreciated through the following illustrative and non-limitative examples.

EXAMPLE 1

Bromine, $H_2O_2$ solution and CAA solution were fed to a 1 l stirred reactor equipped with an overflow discharge. The reaction was exothermic and the reaction mixture was maintained at 88° C.±1° C. by an external thermostat. The clear reaction mixture overflowing from the first stirred reactor was fed to a second stirred reactor maintained at 20° C. A white precipitate was obtained in the second stirred reactor, which precipitate was filtered off and dried without any pretreatment. The dry solid and the mother liquor were analyzed. The reaction conditions and product quantities are set out in Table I-A, and the results of the product analyses in Table I-B below. The mean residence-time ($\tau$) in the first reactor was 12.5 minutes.

EXAMPLE 2

A second reaction cycle was effected by adding CAA to the mother liquor recovered in the reaction of Example 1. The CAA solution so prepared was fed to the reactor and the reaction was carried out as in Example 1, ignoring the residual soluted compounds from the previous cycle. The operating conditions and the results of this experiment are set out in Tables II-A and II-B below.

EXAMPLE 3

Operating as in Example 2, but employing mother liquor recovered from the experiment of Example 2 (cycle 2), a third reaction cycle was carried out. The operating conditions and results of this run are reported in Tables III-A and III-B below.

EXAMPLE 4

Operating as in Example 1, but with a reaction temperature of 90° C.±1° C., a residence time of 9 minutes was allowed in the first reactor. The operating conditions and results of the first reaction cycle of this experiment are set out in Tables IV-A and IV-B.

EXAMPLE 5

A solution of CAA and $NaBrO_3$ (3:1 molar ratio) and bromine were fed to a 1 l stirred reactor equipped with an overflow discharge. The reaction was exothermic and the reaction mixture was maintained at 95° C.±1° C. by an external thermostat. The clear reaction mixture overflowing from the first stirred reactor was fed to a second stirred reactor maintained at 20° C. A white precipitate was obtained in the second stirred reactor, which precipitate was filtered off and dried without any pretreatment. The dry solid and the mother liquor were analyzed. The reaction conditions and product quantities are set out in Table V-A, and the results of the product analyses in Table V-B below. The mean residence-time ($\tau$) in the first reactor was 8-9 minutes.

EXAMPLE 6

A second reaction cycle was effected by adding CAA and $NaBrO_3$ to the mother liquor recovered in the reaction of Example 5. The CAA solution so prepared was fed to the reactor and the reaction was carried out as in Example 5, ignoring the residual soluted compounds from the previous cycle. The operating conditions and the results of this experiment are set out in Tables VI-A and VI-B below.

EXAMPLE 7

Operating as in Example 6, but employing mother liquor recovered from the experiment of Example 6 (cycle 2), a third reaction cycle was carried out. The operating conditions and results of this run are reported in Tables VII-A and VII-B below.

The above description and examples have been provided for the purpose of illustration. Many modifications can be effected in the process of the invention by a skilled person, without exceeding the scope thereof.

TABLE I-A

OPERATING CONDITIONS (Cycle 1)
Continuous Preparation of DBNPA - T = 88° C., $\tau$ = 12.5 min.

| | | FEED RATES | | | | | PRODUCT QUANTITIES | | |
|---|---|---|---|---|---|---|---|---|---|
| | Run[1] | CAA | | $H_2O_2$ | MOLAR RATIO | | | | Dry |
| Sample No. | Time (min) | 7% soln g/min | $Br_2$ g/min | 47.5% g/min | $Br_2$ CAA | $H_2O_2$ CAA | Slurry g | Filtrate g | DBNPA g |
| 1 | 35 | 65.8 | 9.22 | 4.15 | 1.05 | 1.06 | 326.1 | 271.2 | 46.1 |
| 2 | 80 | 65.8 | 9.22 | 4.15 | 1.05 | 1.06 | 43.7 | 36.1 | 6.2 |
| 3 | 110 | 65.2 | 9.92 | 4.74 | 1.14 | 1.22 | 42.9 | 35.9 | 6.1 |
| 4 | 135 | 66.5 | 10.15 | 5.09 | 1.14 | 1.28 | 77.5 | 65.5 | 10.6 |
| 5 | 140 | 65.2 | 9.97 | 5.41 | 1.15 | 1.39 | 599.7 | 500.1 | 82.4 |

TABLE I-B

Product Analyses

| | | FILTRATE ANALYSIS | | | | SOLID ANALYSIS | |
|---|---|---|---|---|---|---|---|
| Sample No. | Yield % | N % | $H_2O_2$ % | [Br] % | $Br^-$ % | N % | Br Active % |
| 1 | 84.4 | 0.36 | 0.56 | 0.65 | 2.1 | 11.4 | 65.7 |
| 2 | 84.6 | 0.36 | 0.54 | 0.45 | 2.4 | 11.4 | 66.2 |
| 3 | 86.4 | 0.30 | 0.86 | 0.53 | 2.3 | 11.6 | 66.1 |
| 4 | 83.4 | 0.36 | 1.02 | 0.54 | 2.3 | 11.6 | 66.1 |
| 5 | 84.2 | 0.35 | 1.11 | 0.64 | 2.0 | 11.6 | 65.7 |

[1]Process time at which collection of the sample started

TABLE II-A

OPERATING CONDITIONS (Cycle 2)
Continuous Preparation of DBNPA in Recycled Mother Liquor - T = 88° C.
$\tau = 12.5$ min.

| Sample No. | Run[1] Time (min) | FEED RATES CAA[2] 7% soln g/min | FEED RATES Br$_2$ g/min | FEED RATES H$_2$O$_2$ 47.5% g/min | MOLAR RATIO Br$_2$ CAA | MOLAR RATIO H$_2$O$_2$ CAA | PRODUCT QUANTITIES Slurry g | PRODUCT QUANTITIES Filtrate g | PRODUCT QUANTITIES Dry DBNPA g |
|---|---|---|---|---|---|---|---|---|---|
| 6 | 0 | 67.8 | 9.95 | 4.46 | 1.10 | 1.10 | 390.5 | 318.0 | 60.2 |
| 7 | 50 | 66.2 | 9.95 | 4.28 | 1.13 | 1.08 | 452.9 | 370.5 | 73.1 |
| 8 | 90 | 65.6 | 9.85 | 4.23 | 1.13 | 1.08 | 95.0 | 76.0 | 15.0 |

TABLE II-B

Product Analyses

| Sample No. | Yield[2] % | FILTRATE ANALYSIS N % | FILTRATE ANALYSIS H$_2$O$_2$ % | FILTRATE ANALYSIS [Br] % | FILTRATE ANALYSIS Br$^-$ % | SOLID ANALYSIS N % | SOLID ANALYSIS Br Active % |
|---|---|---|---|---|---|---|---|
| 6 | 92.7 | 0.53 | 0.96 | 0.62 | 2.3 | 11.4 | 65.6 |
| 7 | 97.2 | 0.44 | 0.94 | 0.70 | 2.2 | 11.5 | 65.7 |
| 8 | 95.1 | 0.48 | 1.00 | 0.63 | 2.4 | 11.5 | 65.4 |

[1]Process time at which collection of the sample started
[2]Not taking into account the residual CAA in the mother liquor (cycle 1, Table I)

TABLE III-A

OPERATING CONDITIONS (Cycle 3)
Continuous Preparation of DBNPA in Recycled Mother Liquor - T = 88° C.
$\tau = 12.5$ min.

| Sample No. | Run[1] Time (min) | FEED RATES CAA[2] 7% soln g/min | FEED RATES Br$_2$ g/min | FEED RATES H$_2$O$_2$ 47.5% g/min | MOLAR RATIO Br$_2$ CAA | MOLAR RATIO H$_2$O$_2$ CAA | PRODUCT QUANTITIES Slurry g | PRODUCT QUANTITIES Filtrate g | PRODUCT QUANTITIES Dry DBNPA g |
|---|---|---|---|---|---|---|---|---|---|
| 9 | 65 | 69.8 | 9.75 | 4.97 | 1.05 | 1.19 | 415.2 | 336.3 | 68.6 |
| 10 | 150 | 68.7 | 9.77 | 4.84 | 1.07 | 1.18 | 167.0 | 136.0 | 28.0 |

TABLE III-B

Product Analyses

| Sample No. | Yield[2] % | FILTRATE ANALYSIS N % | FILTRATE ANALYSIS H$_2$O$_2$ % | FILTRATE ANALYSIS [Br] % | FILTRATE ANALYSIS Br$^-$ % | SOLID ANALYSIS N % | SOLID ANALYSIS Br Active % |
|---|---|---|---|---|---|---|---|
| 9 | 99.2 | 0.47 | 1.1 | 0.70 | 2.2 | 11.6 | 65.9 |
| 10 | 100.8 | 0.43 | 1.0 | 0.66 | 2.3 | 11.6 | 65.2 |

[1]Process time at which collection of the sample started
[2]Not taking into account the residual CAA in the mother liquor (cycle 2, Table II)

TABLE IV-A

OPERATING CONDITIONS (Cycle 1)
Continuous Preparation of DBNPA - T = 90° C., $\tau = 9$ min.

| Sample No. | Run[1] Time (min) | FEED RATES CAA 10% soln g/min | FEED RATES Br$_2$ g/min | FEED RATES H$_2$O$_2$ 51.5% g/min | MOLAR RATIO Br$_2$ CAA | MOLAR RATIO H$_2$O$_2$ CAA | PRODUCT QUANTITIES Slurry g | PRODUCT QUANTITIES Filtrate g | PRODUCT QUANTITIES Dry DBNPA g |
|---|---|---|---|---|---|---|---|---|---|
| 1' | 100 | 66.00 | 15.36 | 6.82 | 1.22 | 1.31 | 343.7 | 272.1 | 59.9 |
| 2' | 140 | 65.65 | 15.29 | 7.16 | 1.22 | 1.39 | 388.5 | 300.3 | 66.4 |
| 3' | 180 | 65.45 | 15.36 | 7.16 | 1.23 | 1.39 | 326.5 | 250.7 | 62.7 |
| 4' | 210 | 65.59 | 15.36 | 7.16 | 1.23 | 1.39 | 307.2 | 235.6 | 58.5 |
| 5' | 330 | 66.69 | 14.95 | 7.23 | 1.18 | 1.38 | 197.0 | 151.5 | 37.5 |

TABLE IV-B

Product Analyses

| Sample No. | Yield % | FILTRATE ANALYSIS N % | FILTRATE ANALYSIS H$_2$O$_2$ % | FILTRATE ANALYSIS [Br] % | FILTRATE ANALYSIS Br$^-$ % | SOLID ANALYSIS N % | SOLID ANALYSIS Br Active % |
|---|---|---|---|---|---|---|---|
| 1' | 80.9 | 0.57 | 1.1 | 0.66 | 2.5 | 11.2 | 66.6 |
| 2' | 79.7 | 0.65 | 1.2 | 0.63 | 2.5 | 11.5 | 66.8 |
| 3' | 89.7 | 0.33 | 1.3 | 0.63 | 2.5 | 11.4 | 66.9 |
| 4' | 88.9 | 0.36 | 1.2 | 0.71 | 2.6 | 11.4 | 66.3 |
| 5' | 88.2 | 0.38 | 1.2 | 0.61 | 2.6 | 11.3 | 66.3 |

[1]Process time at which collection of the sample started

TABLE V-A

OPERATING CONDITIONS (Cycle 1)
Continuous Preparation of DBNPA - T = 95° C., τ = 8-9 min.

| Sample No. | Run[1] Time (min) | FEED RATES CAA 10% soln g/min | $Br_2$ g/min | $NaBrO_3$ g/min | MOLAR RATIO $Br_2$/CAA | $NaBrO_3$/CAA | PRODUCT QUANTITY Dry DBNPA g |
|---|---|---|---|---|---|---|---|
| 1″ | 75 | 65.8 | 13.13 | 3.95 | 1.05 | 1/3 | 84.8 |
| 2″ | 90 | 67.4 | 12.67 | 4.04 | 0.99 | 1/3 | 146.0 |
| 3″ | 115 | 70.8 | 12.88 | 4.25 | 0.96 | 1/3 | 123.9 |
| 4″ | 230 | 70.9 | 13.15 | 4.25 | 0.97 | 1/3 | 109.2 |
| 5″ | 260 | 72.7 | 15.09 | 4.36 | 1.09 | 1/3 | 88.2 |

TABLE V-B

Product Analyses

| Sample No. | Yield % | FILTRATE ANALYSIS N % | $BrO_3^-$ % | [Br] % | $Br^-$ % | SOLID ANALYSIS N % | Br Active % |
|---|---|---|---|---|---|---|---|
| 1″ | 85.0 | 0.61 | 0.5 | 1.3 | 3.1 | 11.5 | 65.4 |
| 2″ | 85.8 | 0.48 | 0.4 | 1.3 | 3.0 | 11.5 | 64.5 |
| 3″ | 86.6 | 0.49 | 0.5 | 1.5 | 3.3 | 11.5 | 66.9 |
| 4″ | 82.8 | 0.65 | 0.5 | 1.8 | 3.4 | 11.5 | 66.0 |
| 5″ | 86.3 | 0.53 | 0.4 | 1.7 | 3.3 | 11.5 | 66.4 |

[1]Process time at which collection of the sample started

TABLE VI-A

OPERATING CONDITIONS (Cycle 2)
Continuous Preparation of DBNPA in Recycled Mother Liquor - T = 95° C., τ = 8-9 min.

| Sample No. | Run[1] Time (min) | FEED RATES CAA 10% soln g/min | $Br_2$ g/min | $NaBrO_3$ g/min | MOLAR RATIO $Br_2$/CAA | $NaBrO_3$/CAA | PRODUCT QUANTITY Dry DBNPA g |
|---|---|---|---|---|---|---|---|
| 6″ | 60 | 67.1 | 12.91 | 4.02 | 1.01 | 1/3 | 54.8 |
| 7″ | 90 | 66.9 | 13.00 | 4.01 | 1.02 | 1/3 | 58.1 |
| 8″ | 120 | 67.1 | 12.65 | 4.02 | 0.99 | 1/3 | 44.4 |

TABLE VI-B

Product Analysis

| Sample No. | Yield % | FILTRATE ANALYSIS N % | $BrO_3^-$ % | [Br] % | $Br^-$ % | SOLID ANALYSIS N % | Br Active % |
|---|---|---|---|---|---|---|---|
| 6″ | 98.0 | 0.63 | 0.5 | 1.2 | 6.2 | 11.4 | 66.0 |
| 7″ | 97.2 | 0.63 | 0.5 | 1.3 | 6.2 | 11.6 | 64.9 |
| 8″ | 92.9 | 0.64 | 0.4 | 1.1 | 6.1 | 11.4 | 65.2 |

[1]Process time at which collection of the sample started
[2]Not taking into account the residual CAA in the mother liquor (cycle 1, Table V)

TABLE VII-A

OPERATING CONDITIONS (Cycle 3)
Continuous Preparation of DBNPA in Recycled Mother Liquor - T = 95° C., τ = 8-9 min.

| Sample No. | Run[1] Time (min) | FEED RATES $CAA^{(2)}$ 10% soln g/min | $Br_2$ g/min | $NaBrO_3$ g/min | MOLAR RATIO $Br_2$/CAA | $NaBrO_3$/CAA | PRODUCT QUANTITY Dry DBNPA g |
|---|---|---|---|---|---|---|---|
| 9″ | 30 | 68.1 | 13.1 | 4.08 | 1.01 | 1/3 | 43.5 |
| 10″ | 50 | 67.2 | 12.7 | 4.03 | 0.99 | 1/3 | 47.2 |
| 11″ | 74 | 69.1 | 13.4 | 4.14 | 1.02 | 1/3 | 46.1 |

TABLE VII-B

Product Analyses

| Sample No. | $Yield^{(2)}$ % | FILTRATE ANALYSIS N % | $BrO_3^-$ % | [Br] % | $Br^-$ % | SOLID ANALYSIS N % | Br Active % |
|---|---|---|---|---|---|---|---|
| 9″ | 102 | 0.81 | 0.5 | 1.1 | 9.4 | 11.1 | 63.6 |
| 10″ | 102 | 0.76 | 0.6 | 1.2 | 9.4 | 11.3 | 63.9 |
| 11″ | 103 | 0.76 | 0.5 | 1.2 | 9.4 | 11.3 | 64.3 |

[1]Process time at which collection of the sample started
[2]Not taking into account the residual CAA in the mother liquor (cycle 2, Table VI)

What we claim is:

1. A process for the preparation of a compound having the formula:

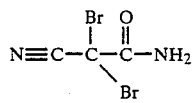

which process comprises:
contacting cyanoacetamide in aqueous solution with bromine or hydrobromic acid, in the presence of an oxidizing agent selected from the group consisting of hydrogen peroxide, $NaBrO_3$, $KBrO_3$, $NaClO_3$ and $KClO_3$, at a temperature above about 70° C.; and cooling said reaction mixture so that said compound is precipitated.

2. A process according to claim 1, wherein the oxidizing agent is hydrogen peroxide.

3. A process according to claim 1, wherein the oxidizing agent is $NaBrO_3$ or $KBrO_3$.

4. A process according to claim 1, wherein the oxidizing agent is $NaClO_3$ or $KClO_3$.

5. A process according to claim 1, wherein the reaction temperature is between about 80° C. and the boiling point of the reaction mixture.

6. A process according to claim 5, wherein the reaction temperature is between about 80° C. and about 100° C.

7. A process according to claim 6, wherein said reaction mixture is cooled to a temperature below about 30° C.

8. A process according to claim 7, wherein said reaction mixture is cooled to a temperature between about 0° C. and about 22° C.

9. A process according to claim 1, wherein said reaction mixture is contacted for a time period less than about 30 minutes.

10. A process according to claim 9, wherein said reaction mixture is contacted for a time period less than about 10 minutes.

11. A process according to claim 1, which further comprises the step of recovering said aqueous solution from said reaction mixture and recycling said recovered aqueous solution for the further preparation of said compound.

12. The process of claim 11, wherein said recovered aqueous solution comprises one or more reaction products and said process further comprises the step of removing a predetermined amount of said recovered aqueous solution prior to said recycling of said recovered aqueous solution so as to prevent the accumulation of said one or more reaction products.

13. The process of claim 12, wherein said one or more reaction products comprises water.

14. The process of claim 12, further comprising the step of adding to said aqueous solution removed from said reaction mixture a predetermined quantity of said compound, so that an aqueous solution of said compound is formed.

* * * * *